US00PP20331P2

(12) United States Plant Patent
Adam, Jr.

(10) Patent No.: US PP20,331 P2
(45) Date of Patent: Sep. 22, 2009

(54) ***PHLOX* PLANT NAMED 'BLUSHING SHORTWOOD'**

(50) Latin Name: *Phlox paniculata*
Varietal Denomination: Blushing Shortwood

(76) Inventor: Sinclair A. Adam, Jr., 231 South Bonsall Rd., Coatesville, PA (US) 19320

( * ) Notice: Subject to any disclaimer, the term of this patent is extended or adjusted under 35 U.S.C. 154(b) by 48 days.

(21) Appl. No.: 12/006,218

(22) Filed: Dec. 31, 2007

(51) Int. Cl.
*A01H 5/00* (2006.01)

(52) U.S. Cl. ..... Plt./320
(58) Field of Classification Search ..... Plt./320
See application file for complete search history.

*Primary Examiner*—Annette H Para
*Assistant Examiner*—Louanne C Krawczewicz Myers
(74) *Attorney, Agent, or Firm*—C. A. Whealy

(57) ABSTRACT

A new and distinct cultivar of *Phlox* plant named 'Blushing Shortwood', characterized by its upright plant habit; freely flowering habit; and white and pale purple bi-colored flowers.

1 Drawing Sheet

Botanical designation: *Phlox paniculata.*
Cultivar denomination: 'Blushing Shortwood'.

BACKGROUND OF THE INVENTION

The present invention relates to a new and distinct cultivar of *Phlox,* botanically known as *Phlox paniculata* and hereinafter referred to by the name 'Blushing Shortwood'.

The new *Phlox* is a naturally-occurring whole plant mutation of the *Phlox paniculata* cultivar Shortwood, disclosed in U.S. Plant Pat. No. 10,379. The new *Phlox* was discovered and selected by the Inventor as a single flowering plant within a population of plants of the cultivar Shortwood in a controlled environment in Coatesville, Pa.

Asexual reproduction of the new *Phlox* by vegetative cuttings in a controlled environment in Lancaster, Pa., has shown that the unique features of this new *Phlox* are stable and reproduced true to type in successive generations.

SUMMARY OF THE INVENTION

The cultivar Blushing Shortwood has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Blushing Shortwood'. These characteristics in combination distinguish 'Blushing Shortwood' as a new and distinct cultivar of *Phlox:*

1. Upright plant habit.
2. Freely flowering habit.
3. White and pale purple bi-colored flowers.

Plants of the new *Phlox* can be compared to plants of the parent, the cultivar Shortwood. Plants of the new *Phlox* differ from plants of the cultivar Shortwood primarily in flower color as plants of the cultivar Shortwood have medium pink-colored flowers with a dark hot pink-colored central "eye".

Plants of the new *Phlox* can also be compared to plants of the cultivar Peppermint Twist, disclosed in U.S. Plant Pat. No. 18,196. Plants of the new *Phlox* and the cultivar Peppermint Twist differ primarily in flower color as plants of the cultivar Peppermint Twist have white and red purple bi-colored flowers.

BRIEF DESCRIPTION OF THE PHOTOGRAPHS

The accompanying colored photographs illustrate the overall appearance of the new *Phlox* showing the colors as true as it is reasonably possible to obtain in colored reproductions of this type. Colors in the photographs may differ slightly from the color values cited in the detailed botanical description which accurately describe the colors of the new *Phlox.*

The photograph at the bottom of the sheet comprises a side perspective view of a typical flowering plant of 'Blushing Shortwood' grown in a container.

The photograph at the top of the sheet is a close-up view of typical flowers of 'Blushing Shortwood'.

DETAILED BOTANICAL DESCRIPTION

The aforementioned photographs and following observations, measurements and values describe plants grown in Lancaster, Pa., under commercial practice during the spring and summer in a polycarbonate-covered greenhouse with day temperatures ranging from 18° C. to 32° C. and night temperatures averaging about 2° C. Plants had been growing for about 1.5 years when the photographs and description were taken. In the following description, color references are made to The Royal Horticultural Society Colour Chart, 1995 Edition, except where general terms of ordinary dictionary significance are used.

Botanical classification: *Phlox paniculata* cultivar Blushing Shortwood.

Parentage: Naturally-occurring whole plant mutation of the *Phlox paniculata* cultivar Shortwood, disclosed in U.S. Plant Pat. No. 10,379.

Propagation:

*Type.*—By vegetative cuttings.

*Time to initiate roots.*—About three to four days at 28° C.

*Time to produce a rooted young plant.*—About 12 to 14 days at 28° C.

*Root description.*—Fibrous.

*Rooting habit.*—Freely branching.

Plant description:

*Plant and growth habit.*—Perennial; upright plant habit; dense and bushy growth habit. Vigorous growth habit. Freely branching habit with about twelve lateral branches developing per plant.

*Plant height.*—About 67 cm.

*Plant diameter.*—About 44 cm.

*Lateral branch description.*—Length: About 65 cm. Diameter: About 6 mm. Internode length: About 1.8 cm. Texture: Pubescent. Strength: Strong. Color: 144A.

Foliage description:

*Arrangement.*—Opposite, simple.

*Length.*—About 11.2 cm.

*Width.*—About 4.2 cm.

*Shape.*—Elliptic.

*Apex.*—Acute.

*Base.*—Truncate.

*Margin.*—Entire; ciliate.

*Texture, upper and lower surfaces.*—Smooth, glabrous; leathery.

*Venation pattern.*—Pinnate; arcuate.

*Color.*—Developing foliage, upper surface: Close to 144A. Developing foliage, lower surface: Close to 146C. Fully expanded foliage, upper surface: Close to 147A; venation, 146B. Fully expanded foliage, lower surface: Close to 147B; venation, 147D.

*Petiole.*—Length: About 5 mm. Diameter: About 2.5 mm. Texture, upper and lower surfaces: Smooth, glabrous. Color, upper surface: Close to 144A. Color, lower surface: Close to 144D.

Flower description:

*Flower arrangement and habit.*—Single rotate flowers arranged in terminal and axillary panicles. Freely flowering habit with about 30 flowers and flower buds per inflorescence. Flowers face upright to outwardly. Flowers slightly fragrant; sweet.

*Natural flowering season.*—Plants of the new *Phlox* flower in June and July in Pennsylvania. Individual flowers last about seven to ten days on the plant; flowers persistent.

*Inflorescence height.*—About 14 cm.

*Inflorescence diameter.*—About 8.8 cm.

*Flower diameter.*—About 2.4 cm.

*Flower length* (*depth*).—About 2.2 cm.

*Throat diameter.*—About 4 mm.

*Tube length.*—About 2 cm.

*Tube diameter.*—About 2 mm.

*Flower bud.*—Shape: Elongated oblong. Length: About 2 cm. Diameter: About 4 mm. Color: Close to 157A.

*Petals.*—Quantity/arrangement: About five arranged in a single whorl, radially symmetrical. Length: About 1.2 cm. Width: About 1.5 cm. Shape: Spatulate. Apex: Rounded. Base: Acute. Margin: Entire. Texture, upper and lower surfaces: Glabrous, smooth; velvety. Texture, throat: Smooth, glabrous. Texture, tube: Pubescent. Color: When opening, upper surface: Close to 157C. When opening, lower surface: Close to 155A. Fully opened, upper surface: Close to 155A tinted with close to 92B to 92C; towards the throat, 1 mm band, 72C; venation, 155A. Fully opened, lower surface: Close to 155A; venation, 155D. Throat: Close to 157A; venation, 145D. Tube: Close to 157B; venation, 145C.

*Sepals.*—Quantity/arrangement: About five arranged in a single whorl; fused at the base. Length: About 6 mm. Width: Less than 1 mm. Shape: Acicular. Apex: Acuminate. Margin: Entire. Texture, upper surface: Glabrous, smooth. Texture, lower surface: Pubescent. Color, upper surface: 145A. Color, lower surface: 146C.

*Peduncles.*—Length: About 2.7 cm. Diameter: About 4 mm. Aspect: Upright to about 45° to 60° from vertical. Texture: Smooth, glabrous. Strength: Strong. Color: 145A.

*Pedicels.*—Length: About 5 mm. Diameter: About 1 mm. Aspect: About 30° from vertical. Texture: Pubescent. Strength: Strong. Color: 146C.

*Reproductive organs.*—Androecium: Stamen number per flower: About five. Anther shape: Oval. Anther size: About 1 mm by 2 mm. Anther color: 160A. Amount of pollen: Moderate. Pollen color: 162D. Gynoecium: Pistil number per flower: One. Pistil length: About 2.7 cm. Stigma shape: Tri-parted. Stigma color: 145A. Style length: About 2.4 mm. Style color: Close to 145C. Ovary color: Close to 144A. Seed/fruit: Seed and fruit development have not been observed on plants of the new *Phlox*.

Garden performance: Plants of the new *Phlox* have been observed to have good garden performance.

Pathogen/pest resistance: Plants of the new *Phlox* have been observed to be resistant to Powdery Mildew. Plants of the new *Phlox* have not been observed to be resistant to pests and other pathogens common to *Phlox*.

It is claimed:

1. A new and distinct *Phlox* plant named 'Blushing Shortwood' as illustrated and described.

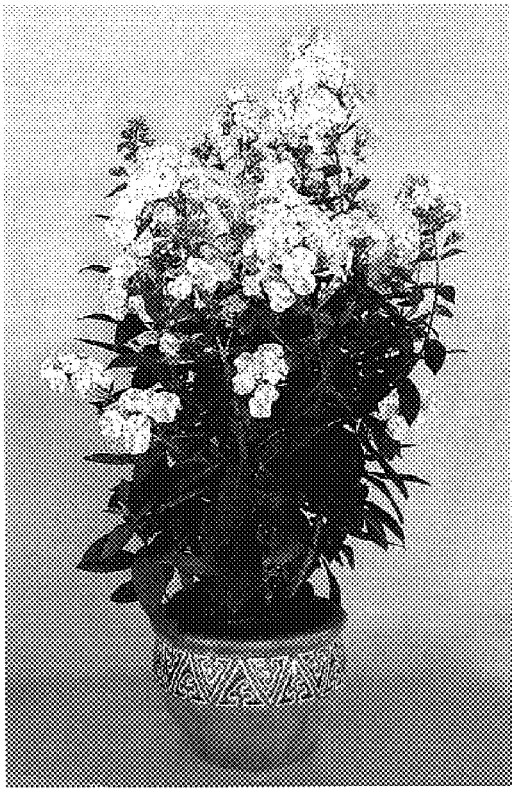
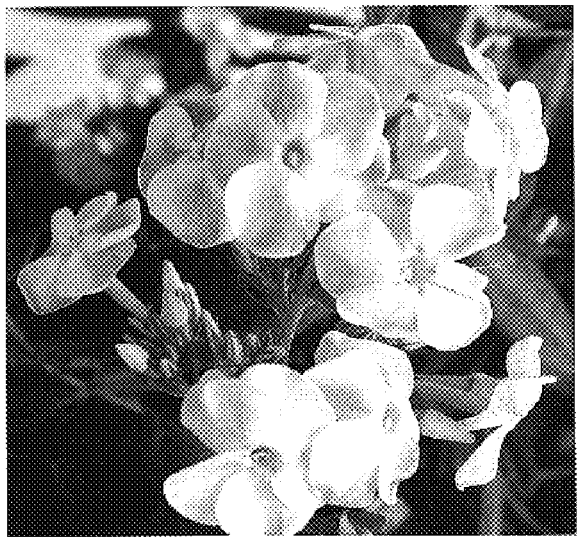

* * * * *